United States Patent [19]

Mixan et al.

[11] 4,209,522
[45] Jun. 24, 1980

[54] ANTIMICROBIAL BIS (5-NITRO-2-THIAZOLYL)THIO)ISO-THIAZOLES AND THIADIAZOLES

[75] Inventors: Craig E. Mixan, Midland; George A. Burk, Bay City, both of Mich.

[73] Assignee: The Dow Chemical Company, Midland, Mich.

[21] Appl. No.: 919,883

[22] Filed: Jun. 28, 1978

[51] Int. Cl.$^2$ .............. A01N 9/12; A61L 13/00; C07D 417/14
[52] U.S. Cl. .................. 424/270; 548/130; 548/142; 548/184; 106/18.33
[58] Field of Search ............ 260/302.5 D, 302 S, 260/302 H; 424/270

[56] References Cited

U.S. PATENT DOCUMENTS

| | | | |
|---|---|---|---|
| 3,155,678 | 11/1964 | Hatchand | 260/302 S |
| 3,230,229 | 1/1966 | Hatchand | 260/302 S |
| 3,597,426 | 8/1971 | Seltzer | 260/302 H |
| 3,634,443 | 1/1972 | Schmidt et al. | 260/302 S |
| 3,839,348 | 10/1974 | Elslager et al. | 260/302 S |
| 3,850,939 | 11/1974 | Elslager et al. | 260/302 S |
| 3,870,725 | 3/1975 | Hughes et al. | 260/302 H |

*Primary Examiner*—Alton D. Rollins

[57] ABSTRACT

The novel compounds corresponding to the formula

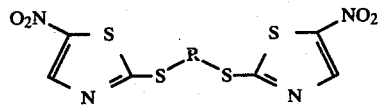

or of the formula

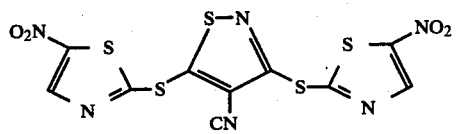

wherein R is a thiadiazole radical. These compounds exhibit utility in the control and kill of bacteria and fungi.

6 Claims, No Drawings

ANTIMICROBIAL BIS(5-NITRO-2-THIAZOLYL)THIOISOTHIAZOLES AND THIADIAZOLES

SUMMARY OF THE INVENTION

The novel compounds of the present invention, hereinafter alternatively referred to as "active compounds", correspond to the formula

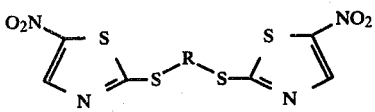

or of the formula

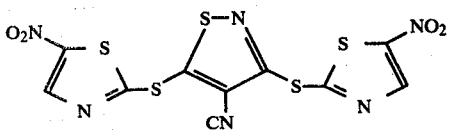

wherein R is a thiadiazole radical.

The active compounds, directly or as active ingredients in formulations and compositions, exhibit, when used in antimicrobially effective amounts, antimicrobial activity against fungi and bacteria. Hereinafter the terms "antimicrobial" and "antimicrobially effective" when used in conjunction with the active compounds will be employed to identify their activity against fungi and/or bacteria.

The invention's novel bis((5-nitro-2-thiazolyl)thio)isothiazoles and thiadiazole are prepared by the reaction of the corresponding di(sodiomercapto) isothiazole or thiadiazole and 2-bromo-5-nitrothiazole in methanol. The reaction mixture is maintained at about 20° C. to about 60° C., with agitation until substantial completion of the reaction, usually from about 1 to about 4 hours. The product compound is recovered by filtration, washed with water and methanol and dried and, if desired, can be further purified by conventional techniques known to those in the art.

It is preferred that, in the above-reaction, the molar proportions of nitrothiazole starting material to either the isothiazole or thiadiazole starting material is at least 2 or 1.

The term "thiadiazole radical", as used in the present specification and claims, refers to either a 1,2,4-thiadiazole or a 1,3,4-thiadiazole radical.

DESCRIPTION OF THE PREFERRED EMBODIMENTS

The following examples and teachings illustrate the present invention and the manner by which it can be practiced but as such should not be construed as limitations upon the overall scope of the same. The product compounds are identified by elemental analysis, nuclear magnetic resonance spectroscopy (NMR) and infrared spectroscopy (IR).

EXAMPLE 1—Preparation of 3,5-bis((5-nitro-2-thiazolyl)thio)-4-isothiazolecarbonitrile (Compound 1)

To a solution of 4.36 (0.02 mol.) of 3,5-di(sodiomercapto)-4-isothiazole carbonitrile in methanol was added 8.4 g (0.04 mol.) of 2-bromo-5-nitrothiazole. A yellow-brown solid begins to precipitate almost immediately. The reaction mixture is stirred for an additional 2 hours at room temperature (∼22° C.). The precipitate is collected by suction filtration, washed with water and methanol and dried in vacuo to yield 6.77 g (79% yield from the isothiazole) of a tan solid, m.p. 197°–199.5° C.

A sample of Compound 1 was subjected to elemental analysis. The results obtained were as follows:

Analysis for $C_{10}H_2N_6O_4S_5$: Calcd: C, 27.91; H, 0.47; N, 19.53. Found: C, 27.60; H, 0.77; N, 19.02.

IR confirmed the assigned structure:

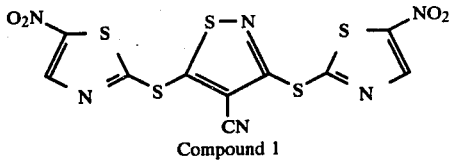

Compound 1

The following compounds of Examples 2 and 3 were prepared by the procedures of Example 1 by substituting a corresponding thiadiazole starting material for the isothiazole starting material used in the procedure of Example 1. The product compounds were identified by elemental analysis. In each of these Examples IR confirmed the assigned structure.

EXAMPLE 2
2,5-bis((5-nitro-2-thiazolyl)thio)-1,3,4-thiadiazole (Compound 2)

The product compound was prepared from 2,5-di(sodiomercapto)-1,3,4-thiadiazole for a 80% yield of a light yellow solid, m.p. 152°–153° C.:

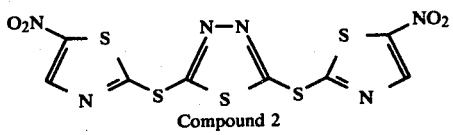

Compound 2

Analysis for $C_8H_2N_6O_4S_5$: Calcd: C, 23.65; H, 0.50; N, 20.65. Found: C, 23.40; H, 0.66; N, 20.95.

EXAMPLE 3
3,5-bis((5-nitro-2-thiazolyl)thio)-1,2,4-thiadiazole (Compound 3)

The product compound was prepared from 3,5-di(sodiomercapto)-1,2,4-thiadiazole for a 70% yield of a yellow solid, m.p. 157°–158° C.:

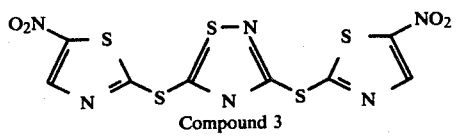

Compound 3

Analysis for $C_8H_2N_6O_4S_5$: Calcd: C, 23.65; H, 0.50; N, 20.65. Found: C, 24.00; H, 0.87; N, 18.90.

The active compounds of the invention are suitable for use as antimicrobials for the control of bacteria and fungi. This is not to suggest that the active compounds and mixtures thereof with usual additives are equally effective against all such organisms at the same concentration. For such uses, the active compounds can be employed in an unmodified form or dispersed on a finely divided solid and employed as a dust. Such mixtures can also be dispersed in water with the aid of a surface-active agent and the resulting emulsion employed as a spray. In other procedures, the active compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good control and kill have been realized against a number of representative organisms with compositions wherein antimicrobially-effective amounts of from about 1 to about 500 parts by weight of one or more of the active compounds per million parts of such compositions are employed. As stated hereinbefore the active antimicrobially-effective amount to be employed against a given organism or in a certain composition can readily be determined by one skilled in the art.

Incorporation of the active compounds of this invention into materials which are subject to fungal attack inhibits the growth of the fungi and preserves the original value of the materials. The active compounds are sufficiently nonvolatile and water-insoluble so that they will persist on or in such materials for long periods of time. Examples of materials which are adversely affected by fungal growth are latex and alkyl paint films, wood and wooden products. The active compounds are sufficiently active against fungi such that only small quantities are required to prevent mildew on paint films or wood rot. The active compounds are therefore useful for long-term protection against fungal growth in or on materials having a wood basis or a protective or decorative paint film or other coating or covering subject to fungal attack.

In a standard activity test, samples of each of Compounds 1 thru 3 were individually dispersed in warm melted nutrient agar which was poured into petri dishes and allowed to solidify, the active compounds being employed in an amount sufficient to provide from 1 to 500 parts by weight thereof per million parts (ppm) of the ultimate agar composition. The surface of the agar was inoculated with a variety of bacterial and fungal pest organisms, and the inoculated plates incubated under conditions conducive to bacterial and fungal growth. Similar check plates in which the agar did not contain the active compounds or other toxic compounds were similarly inoculated and incubated.

In these studies, Compounds 1 thru 3 gave 100% growth inhibition (kill) and control of the following organisms at the indicated concentrations in part per million (ppm):

TABLE

| ANTIMICROBIAL ACTIVITY | | | |
|---|---|---|---|
| | Concentration in ppm | | |
| Organism | Compound 1 | Compound 2 | Compound 3 |
| S. aureus | 500 | 5 | 5 |
| S. typhosa | 500 | 5 | 100 |
| A. aerogenes | * | * | 500 |
| P. aeruginosa | * | 500 | * |
| Pseudomonas sp. strain 10 | * | 500 | 500 |
| B. subtilis | 500 | 1 | 5 |
| K. Pneumoniae M-1 | * | * | 500 |
| S. marcesens | * | * | 500 |
| C. albicans N | * | 5 | 50 |
| C. albicans D | * | 500 | 50 |
| C. pelliculosa | * | 100 | 50 |
| Torulopsis specie | * | * | 50 |
| P. Pullulans | 500 | 500 | 50 |
| C. ips | 500 | 500 | 50 |
| T. mentagrophytes | 500 | 50 | 500 |
| P. chrysogesum | 500 | 100 | 1 |
| Tri-sp-mad-P-42 | * | * | 100 |
| A. Fumigatus | 500 | 500 | 10 |
| A. niger | 500 | 500 | 50 |

*no kill at 500 ppm

Preparation of the Starting Materials

The isothiazole starting material may be prepared according to the method taught by W. R. Hatchard, *J. Org. Chemistry*, 28, 2163 (1963). 3,5-Di(sodiomercapto)-1,2,4-thiadiazole may be prepared according to the method taught by Raymond Seltzer, *J. Org. Chemistry*, 34, 2562 (1969). 2,5-Di(sodiomercapto)-1,3,4-thiadiazole and 2-bromo-5-nitrothiazole are available commercially.

What is claimed is:
1. A compound of the formula

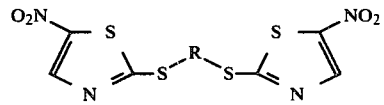

or of the formula

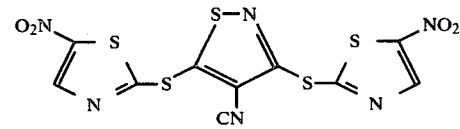

wherein R is the thiadiazole radical.

2. The compound of claim 1 which is 3,5-bis((5-nitro-2-thiazolyl)thio)-4-isothiazolecarbonitrile.

3. The compound of claim 1 which is 2,5-bis((5-nitro-2-thiazolyl)thio)-1,3,4-thiadiazole.

4. The compound of claim 1 which is 3,5-bis((5-nitro-2-thiazolyl)thio)1,2,4-thiadiazole.

5. A method for controlling bacteria and fungi which comprises applying to said bacteria and fungi or their habitat an antimicrobially-effective amount of a compound of claim 1.

6. A composition for controlling bacteria and fungi comprising an antimicrobially-effective amount of a compound of claim 1 in combination with a solid or liquid diluent medium.

* * * * *